United States Patent [19]

Takahashi

[11] 4,325,028
[45] Apr. 13, 1982

[54] EXAMINATION APPARATUS FOR MILK DRAWN FROM QUARTER MAMMAE OF A MILK COW

[75] Inventor: Toshio Takahashi, Honjo, Japan

[73] Assignee: Eisai Co., Ltd., Tokyo, Japan

[21] Appl. No.: 191,213

[22] PCT Filed: Jul. 13, 1979

[86] PCT No.: PCT/JP79/00187

§ 371 Date: Mar. 14, 1980

§ 102(e) Date: Mar. 5, 1980

[87] PCT Pub. No.: WO80/00274

PCT Pub. Date: Feb. 21, 1980

[30] Foreign Application Priority Data

Jul. 14, 1978 [JP] Japan .................. 53-085951

[51] Int. Cl.$^3$ .............................. G01N 27/42
[52] U.S. Cl. .................. 324/442; 119/14.14
[58] Field of Search .............. 324/442, 443; 119/14.14

[56] References Cited

U.S. PATENT DOCUMENTS

| | | | |
|---|---|---|---|
| 2,898,549 | 8/1959 | Miller | 324/443 |
| 3,358,223 | 12/1967 | Birnstingl | 324/442 |
| 3,512,080 | 5/1970 | Hanson | 324/443 |
| 3,664,306 | 5/1972 | Quayle | 324/443 |
| 3,762,371 | 10/1973 | Quayle | 324/443 |

Primary Examiner—Michael J. Tokar
Attorney, Agent, or Firm—Blanchard, Flynn, Thiel, Boutell & Tanis

[57] ABSTRACT

In every flow passage of milk sucked out from each quarter mamma through each teatcup, a trap is equipped. The electric conductivity of the milk is measured independently by means of electrodes equipped in each trap.

The difference in value among quarter mammae is obtained by performing a subtraction between the minimum conductivity selected out among these traps and the other conductivity values.

Said differential value is compared with predetermined reference values. The outputs of comparator circuits are divided into three groups. When the output of any one group is below a lower limit value, the milk which gives such output is indicated as normal. If the output is higher than an upper limit value, the milk is indicated as abnormal, and when intermediate these limits, an indication of quasi-abnormality is given. Especially for abnormal and quasi-abnormal milk a warning is given by sounding a buzzer.

10 Claims, 4 Drawing Figures

EXAMINATION APPARATUS FOR MILK DRAWN FROM QUARTER MAMMAE OF A MILK COW

FIELD OF THE INVENTION

The present invention relates to an examination apparatus for milk drawn from quarter mammae of a milk cow for examining whether the cow is suffering from mastitis or not and the extent of the disease, during a milking operation.

Particularly, the present invention relates to an examination apparatus for milk drawn from the quarter mammae which measures the electric conductivity of the milk by measuring electrodes equipped between four teatcups of a milking machine and the milk claw in which milk sucked out from four quarter mammae is joined, and compares the difference in value between the electric conductivity measured for each mamma milk and a predetermined reference value for checking whether there is abnormality in the milk drawn from each quarter mamma or not.

BACKGROUND OF THE INVENTION

When a milk cow suffers from mastitis or milk fever, the deterioration of milk and the decrease of the quantity of secreted milk inflict heavy loss on the milk producer. Therefore, the early discovery of mastitis of the cow is important.

At present, the abnormal milk detection method being utilized most widely is the California Mastitis Test (CMT) or a modification of CMT.

The extent of a coagulation reaction caused when CMT reagent is added to the sample milk is judged by this method. This is to measure semiqualitatively the number of somatic cell (mainly leukocytes) included in the milk.

However, these test operations require experience, being defective in that the judgement is apt to be governed by subjective elements, the difference between individuals, or the physiological condition of the cow. Therefore a correct judgement cannot be done easily.

It is well known that mastitis and milk fever are diseases of mamma and in the milk drawn from a cow suffering from these diseases, the concentration of Na ion and Cl ion is abnormally high, increasing the electric conductivity of the milk.

According to the results of observation of values of ingredients analysed of milk from each quarter mamma, the ingredient of milk from each quarter mamma of the same udder of a healthy cow is the same, showing the same electric conductivity. However, in case the cow is suffering from mastitis it is scarcely observed that all milk from four quarter mammae are tainted and the ingredients of milk from all quarter mammae show abnormal values. The abnormality is usually restricted to some of the quarter mammae. This is because quarter mammae do not have the same sensitivity to various stimulations and a certain quarter mamma is more affected sensitively than other quarter mamma, being apt to suffer from the mastitis easily.

Accordingly, it is necessary to examine the milk drawn from each quarter mamma instead of the mixed milk from four quarter mammae and to measure the electric conductivity of the milk from each quarter mamma. The electric conductivity of the milk is varied not only by the disease, such as mastitis, but also by the difference of the individual cow, the cow's physiological condition, the season and the temperature. Therefore, by comparing the conductivity of respective milk drawn from the quarter mammae, the mastitis can be surely judged. At the same the extent of trouble existing in each quarter mamma can be ascertained.

The judging method by means of the electric conductivity measurement is to measure the specific electric conductivity of milk from four quarter mammae, obtaining the difference of the specific conductivity between the reference milk from a quarter mamma (the milk from the quarter mamma showing the minimum specific electric conductivity) and the milk from other quarter mamma. The milk showing a difference in value of the specific electric conductivity between the quarter mammae larger than the abnormal milk detection reference value is judged to be the milk drawn from an abnormal quarter mamma and the quarter mamma secreting such milk is judged to be suffering from the mastitis. The extent of disease is proportional to the difference in value between quarter mammae.

This method does not depend on any individual difference in the extent of coagulation of the milk to be examined, the observational distinction of tone of color and the like, compared with said CMT tester method which has been carried out. Thus this method is extremely effective because it is sharp in the examination sensitivity.

The electric conductivity measuring method, like the conventional CMT tester method, is inconvenient in that a certain fixed quantity of milk sucked from each quarter mamma must be sampled individually for the examination and only the state at a certain time point can be examined. Therefore a continuous examination cannot be done during the whole milking operation.

Generally, in the milking operation, milk secreted in each quarter mamma automatically drawn by a milking machine is mixed immediately. Therefore, the sampling is necessary to be done before the milking machine is fitted to the cow. Further, the state of the quality of milk changing during the operation of milking cannot be checked.

The object of the present invention is to check milk drawn from each quarter mamma automatically and continuously during the continuous milking operation by using the examination apparatus for milk from individual quarter mamma to effect electric conductivity measurement in the milking process.

Further, the object of the present invention is to indicate the extent of the quality of milk in multiple stages by dividing the output obtained through the mesurement into some groups.

SUMMARY OF THE INVENTION

An examination apparatus according to the present invention is provided between a teatcup of the milking machine and a milkclaw where milk from four quarter mammae join together or is provided within the milkclaw itself, and comprises four traps each of which has measuring electrodes, an electric conductivity measuring circuit connected to said measuring electrode, a comparator circuit group for comparing differences between each quarter mamma and a reference value and indication members for indicating the extent of disease of the cow.

In each trap described above, a certain quantity of milk drawn from each quarter mamma is always stored in such a way that the stored milk is exchanged successively with milk newly sucked out.

Accordingly even though the milk from each quarter mamma is drawn out intermittently by the intermittent vacuum sucking of the milking machine, the measuring electrode is always dipped into the milk from each quarter mamma which is the object to be examined, being protected from a wrong examination due to intermission or bubble of the milk from the quarter mamma.

In each one of said four traps there is a pair of measuring electrodes of metal such as platinum, stainless steel and the like. These are electrically insulated from each other, and produce output signals corresponding to the electrical conductivity of the milk from the quarter mamma when an AC input signal with a constant amplitude is applied.

Said measuring circuit receives output signals from four sets of measuring electrodes, generating signals for the value of the electric conductivity of milk from each quarter mamma. The lowest value is picked up as the reference value. Other values are compared with the reference value for obtaining respective value differences. Indication lamps indicate for each quarter mamma to which level group, among a plural number of predetermined level groups, these value differences belong. If the value of difference exceeds the predetermined level, the warning is given by an alarm buzzer. Thus, the milker can see whether the abnormality is caused or not by the buzzer and recognize which quarter mamma is abnormal seeing the indication lamp. Therefore, the milker can detect the abnormal milk and practice an early countermeasure for treating the cow suffering from the disease, thus obtaining an extremely economical effect.

DETAILED DESCRIPTION

Figure 1:
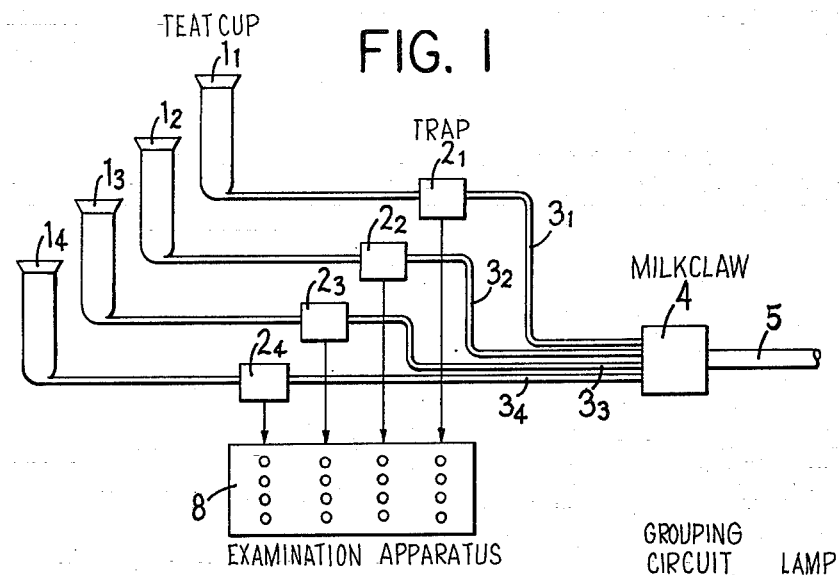
FIG. 1 shows a schematic view of a preferred embodiment of the examination apparatus for milk from the quarter mamma according to the present invention.

Hereinafter, the preferred embodiment of the present invention will be described referring to the drawings.

Figure 2:
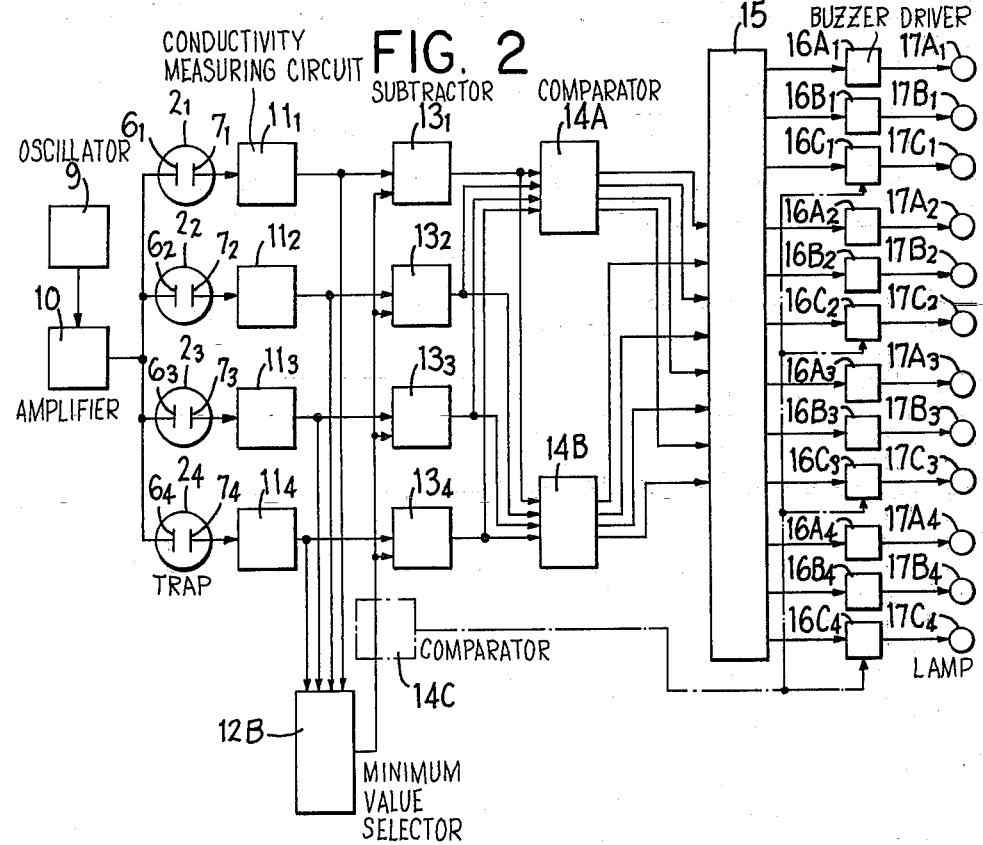
FIG. 2 is a block diagram of the examination apparatus shown in FIG. 1.

In FIG. 1, ($1_1$), ($1_2$), ($1_3$) and ($1_4$) are teatcups to be fitted to the mammae of a milk cow. These teatcups are connected to a milkclaw (4) through flow ways ($3_1$), ($3_2$), ($3_3$) and ($3_4$) with respective traps ($2_1$), ($2_2$), ($2_3$) and ($2_4$). In the milkclaw (4), milk from the respective quarter mamma is joined and sent to a transmitting pipe (5). Referring to FIG. 2, in each one of said traps are fitted a pair of metallic electrodes ($6_1$) and ($7_1$), ($6_2$) and ($7_2$), ($6_3$) and ($7_3$), and ($6_4$) and ($7_4$), which are harmless to men for reason of sanitation. These electrodes are connected to an examination apparatus (8). In FIG. 2 showing the detail of the examination apparatus, a sinusoidal wave oscillation circuit (9) is connected to each one of electrodes ($6_1$), ($6_2$), ($6_3$) and ($6_4$) on one side of said traps through a buffer amplifier (10).

Each one of the electrodes on the other side ($7_1$), ($7_2$), ($7_3$) and ($7_4$) is connected to one of four electric conductivity measuring circuits ($11_1$), ($11_2$), ($11_3$) and ($11_4$). These measuring circuits are connected to a minimum value selection circuit (12B) and subtraction circuits ($13_1$), ($13_2$), ($13_3$) and ($13_4$). These subtraction circuits ($13_1$), ($13_2$), ($13_3$) and ($13_4$) are connected through comparator circuits (14A), and (14B) and a grouping circuit (15) to lamp and buzzer driving circuits ($16A_1$), ($16B_1$) and ($16C_1$), ($16A_2$), ($16B_2$), and ($16C_2$), ($16A_3$), and ($16B_3$) and ($16C_3$), and ($16A_4$), ($16B_4$) and ($16C_4$), and also to indication lamps ($17A_1$), ($17B_1$) and ($17C_1$), ($17A_2$), ($17B_2$) and ($17C_2$), ($17A_3$), ($17B_3$) and ($17C_3$), and ($17A_4$), ($17B_4$) and ($17C_4$).

Figure 3:
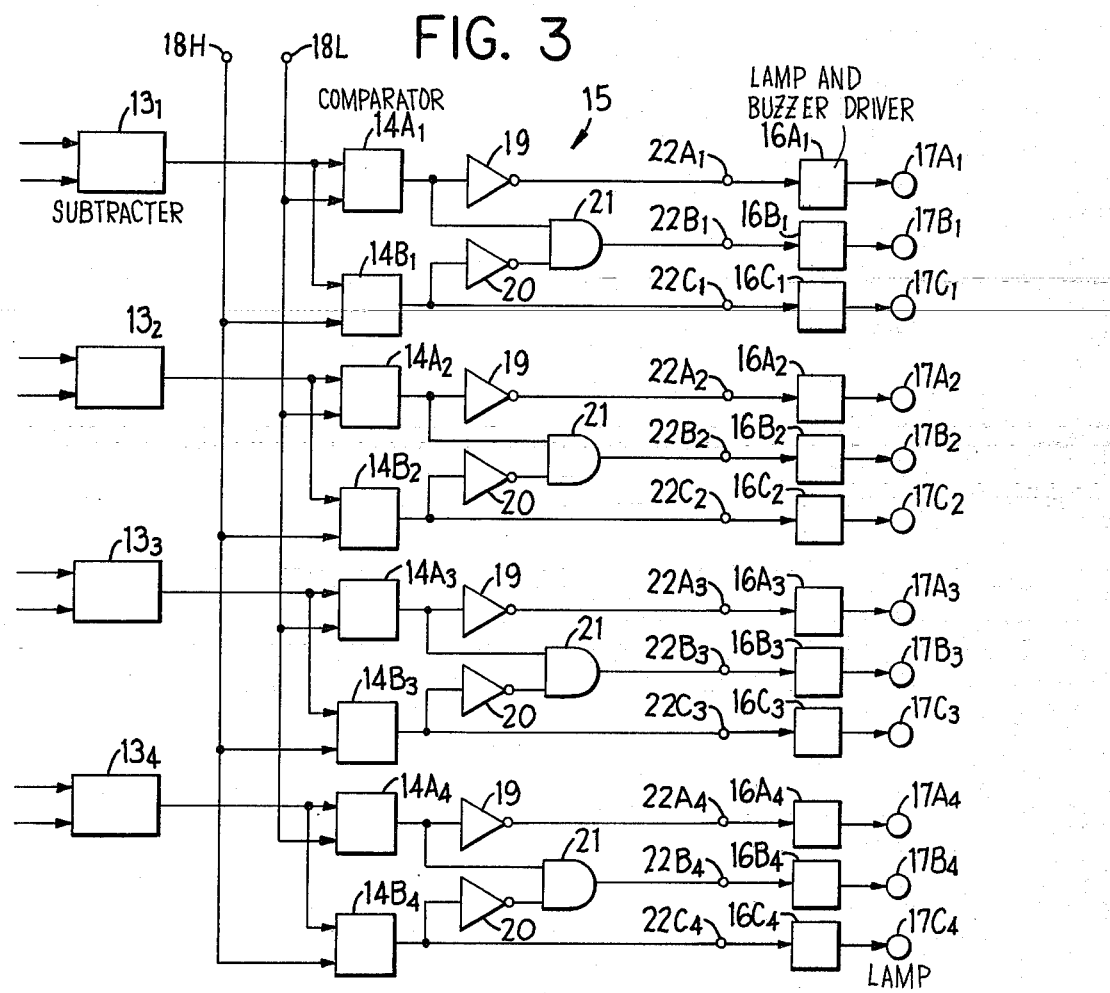
FIG. 3 is a circuit diagram of a grouping circuit in FIG. 2.

Said comparator circuits and lamp and buzzer driving circuits ($16A_1$), ($16B_1$), ($16C_1$), ..., ($16A_4$), ($16B_4$), ($16C_4$) are constructed as shown in FIG. 3. That is, a low level reference value inputting terminal (18L) is connected to one of the group of comparator circuits ($14A_1$), ($14A_2$) ($14A_3$) and ($14A_4$), while a high level reference value inputting terminal (18H) is connected to the other group of comparator circuits ($14B_1$), ($14B_2$), ($14B_3$) and ($14B_4$). The grouping circuit (15) is composed of sets of two NOT circuits (19) and (20) and one AND circuit (21). At the first output terminals ($22A_1$), ($22A_2$), ($22A_3$) and ($22A_4$), signals of the normal milk are outputted, at the 2nd output terminals ($22B_1$), ($22B_2$), ($22B_3$) and ($22B_4$) signals of the quasi-abnormal milk (there is doubt that the milk is abnormal) are outputted and at the 3rd output terminals ($22C_1$), ($22C_2$), ($22C_3$) and ($22C_4$), signals of abnormal milk are outputted. These 1st, 2nd and 3rd output terminals ($22A_1$), ($22A_2$), ($22A_3$) and ($22A_4$), ($22B_1$), ($22B_2$), ($22B_3$) and ($22B_4$) and ($22C_1$), ($22C_2$), ($22C_3$) and ($22C_4$) are connected to normal milk indication lamps ($17A_1$), ($17A_2$), ($17A_3$) and ($17A_4$), quasi-abnormal milk indication lamps ($17B_1$), ($17B_2$), ($17B_3$) and ($17B_4$), and abnormal milk indicator lamps ($17C_1$), ($17C_2$), ($17C_3$) and ($17C_4$) through said driving circuits ($16A_1$) ..., ($16B_1$) ..., ($16C_1$) ..., ($16C_4$). Although the buzzer is not shown, it sounds when at any one of the 2nd or the 3rd terminals ($22B_1$) ... ($22B_4$), and ($22C_1$) ... ($24C_4$) the output appears.

The action of the present invention will be described hereinafter.

As the reference values applied to the lower level input terminal (18L) and the higher level input terminal (18H), $5 \times 10^{-4}$ S/cm and $15 \times 10^{-4}$ S/cm are taken respectively. Accordingly, the milk with a measured value lower than $5 \times 10^{-4}$ S/cm is judged to be normal, while that higher than $15 \times 10^{-4}$ S/cm being judged to be abnormal, and further the milk having a value between these two being judged to be quasi-abnormal, where S (siemens) indicates $\mho$ (mho).

In the state established as described above, when the milk is vacuum-sucked intermittently by the milking machine from the side of milkclaw (4), milk from teatcups ($1_1$), ($1_2$), ($1_3$) and ($1_4$) passing through flow ways ($3_1$), ($3_2$), ($3_3$) and ($3_4$) is stored for a time in each one of traps ($2_1$), ($2_2$), ($2_3$) and ($2_4$), and is then being joint together in the milkclaw (4).

The sinusoidal output signal from the oscillation circuit (9) is applied to each one of electrodes ($6_1$), ($6_2$), ($6_3$) and ($6_4$) on one side through the buffer amplifier (10), and an alternating current flows to each one of electrodes ($7_1$), ($7_2$), ($7_3$) and ($7_4$) on the other side corresponding to the electric conductivity of milk from each one of quarter mammae in respective traps ($2_1$), ($2_2$), ($2_3$), and ($2_4$). In each one of conductivity measuring circuits ($11_1$), ($11_2$), ($11_3$) and ($11_4$), a DC signal showing the electric conductivity of milk from a quarter mamma is taken out as an output. These four signals showing the electric conductivity are transmitted to a minimum value selection circuit (12B), and from among these signals the minimum conductivity signal is selected. In subtraction circuits $(13_1)$, $(13_2)$, $(13_3)$ and $(13_4)$, the subtraction is performed between the minimum conductivity and each conductivity. From each circuit a signal of differential conductivity is outputted. The differential conductivity in one group of comparator circuits $(14A_1)$, $(14A_2)$, $(14A_3)$ and $(14A_4)$ is compared with the reference value at the lower level, that is $5 \times 10^{-4}$ S/cm. When the former is higher than the latter, an output appears. In the other group of comparator circuits $(14B_1)$, $(14B_2)$, $(14B_3)$ and $(14B_4)$, the comparison is performed with the higher level reference value $15 \times 10^{-4}$ S/cm. If the differential is lower than this, an output appears. The output signals from groups of comparators $(14A_1)$, $(14A_2)$, $(14A_3)$ and $(14A_4)$, $(14B_1)$, $(14B_2)$, $(14B_3)$ and $(14B_4)$ are transmitted to the grouping circuit (15) in which signals are divided into three groups. In other words, when there is no output from one group of comparator circuits $(14A_1)$, $(14A_2)$, $(14A_3)$ and $(14A_4)$, outputs appear only at the 1st output terminals $(22A_1)$, $(22A_2)$, $(22A_3)$ and $(22A_4)$ through NOT circuits (19), (19), (19) and (19), driving driving circuits $(16A_1)$, $(16A_2)$, $(16A_3)$ and $(16A_4)$ and lighting normal milk indication lamps $(17A_1)$, $(17A_2)$, $(17A_3)$ and $(17A_4)$. Next, when there appear outputs only from one group of comparator circuits $(14A_1)$, $(14A_2)$, $(14A_3)$ and $(14A_4)$ and there is no output from the other group of comparator circuits $(14B_1)$, $(14B_2)$, $(14B_3)$ and $(14B_4)$, signals from the one group of the comparator circuits $(14A_1)$, $(14A_2)$, $(14A_3)$ and $(14A_4)$ are applied to respective input terminals of the AND circuits 21 on the one side and signals inverted by NOT circuits (20), (20), (20) and (20) are applied to respective terminals on the other side of said AND circuits. Therefore, outputs come out only from the 2nd terminals $(22B_1)$, $(22B_2)$, $(22B_3)$ and $(22B_4)$, driving the driving circuits $(16B_1)$, $(16B_2)$, $(16B_3)$ and $(16B_4)$, and lighting the quasi-abnormal milk indication lamps $(17B_1)$, $(17B_2)$, $(17B_3)$ and $(17B_4)$ and at the same time sounding the buzzer. Further, when there are outputs from both groups of comparator circuits $(14A_1)$, $(14A_2)$, $(14A_3)$ and $(14A_4)$, and $(14B_1)$, $(14B_2)$, $(14B_3)$ and $(14B_4)$, the outputs come out only from the 3rd output terminals $(22C_1)$, $(22C_2)$, $(22C_3)$ and $(22C_4)$, driving the driving circuits $(16C_1)$, $(16C_2)$, $(16C_3)$ and $(16C_4)$, lighting the abnormal milk indication lamps $(17C_1)$, $(17C_2)$, $(17C_3)$ and $(17C_4)$ and sounding the buzzer.

Thus, which milk from quarter mamma is normal, quasi-normal or abnormal is individually indicated and the extent of quality of milk is judged.

In the above mentioned embodiment, the examination apparatus is so constructed as to judge the milk from the quarter mammae individually. It is because when the milk cow suffers from disease such as mastitis or heat fever, normally all of the quarter mamma do not suffer at the same time, but in most cases only one or two of the quarter mammae suffer. Therefore, if any one of the quarter mammae suffering can be found, the milking operation can be ceased and the proper treatment can be taken.

To judge whether the milk from the quarter mamma is normal or not (abnormal) is important and profitable to carry on an enterprise in the livestock farming.

Figure 4:
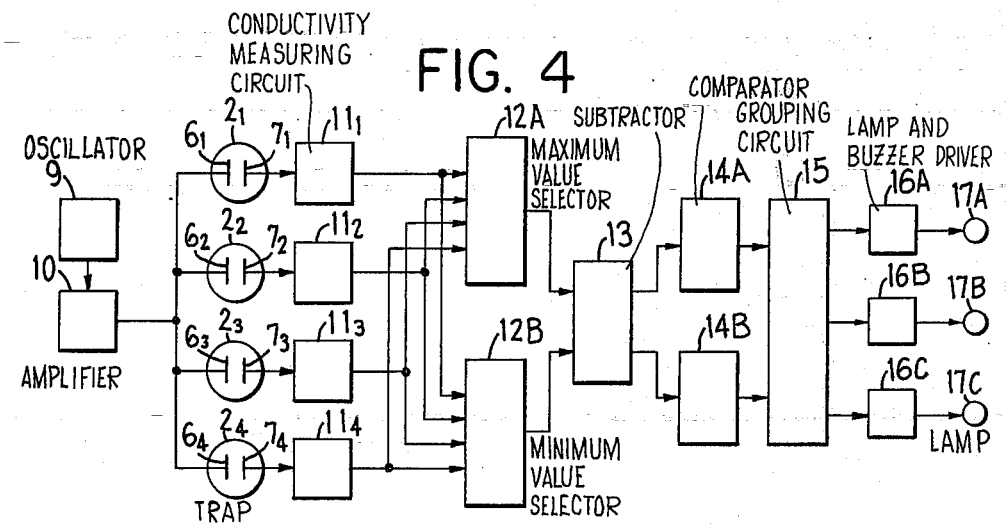
FIG. 4 is a block diagram of another embodiment of the examination apparatus.

However, even when any one of milk from the quarter mammae is abnormal, if the apparatus can judge the milk to be abnormal, the object of the present invention can be attained. Accordingly, for attaining the object the apparatus may be constructed as shown in FIG. 4.

The maximum value and the minimum value of the electrical conductivity among values of electric conductivity of cow's milk from the quarter mammae are selected by respective selection circuits (12A) and (12B). These values selected are inputted to a subtraction circuit (13) for subtracting and the differential value of the conductivity is output. And then as described hitherto, signals showing to what range the milk from the quarter mamma belongs are outputted by the group of comparator circuits (14A) and (14B) and the grouping circuit (15), and it is easily judged whether the cow whose milk is being measured suffers from the disease such as mastitis or milk fever.

In said embodiment, although the grouping circuit is composed of two NOT circuits and one AND circuit, it is not restricted to construct the grouping circuit in such a way but a matrix circuit may be employed.

In FIG. 2, among outputs from the conductivity measuring circuits $(11_1)$, $(11_2)$, $(11_3)$ and $(11_4)$, the minimum conductivity value obtained in the minimum selection circuit (12B) is to be transmitted to the subtraction circuits $(13_1)$, $(13_2)$, $(13_3)$ and $(13_4)$ as it is for obtaining the differential value. In many cases, it is observed that the abnormality is found in the limited portion among four quarter mammae as described above.

Rarely do all of four quarter mammae suffer and milks from these mammae show respectively high conductivity values and give almost no difference to the differential value among quarter mammae.

Furthermore, as shown in FIG. 2 by chain lines, by inserting the comparator circuit (14C) in which the abnormal milk judging reference value is already set to the minimum value selection circuit (12B), when the minimum conductivity value obtained by the minimum selection circuit (12B) exceeds the reference value of this comparator circuit (14C), all the milk from the quarter mammae are considered to be abnormal ones which show abnormally high conductivity and the comparator circuit (14) is connected to the lamp and buzzer drivng circuits $(16C_1)$, $(16C_2)$, $(16C_3)$ and $(16C_4)$, directly actuating the abnormal milk indication lamps $(17C_1)$, $(17C_2)$, $(17C_3)$ and $(17C_4)$. When the value of the min. value selection circuit (12B) does not exceed the reference value of the comparator circuit (14C), the signal from the selection circuit (12B) is transmitted to subtraction circuits $(13_1)$, $(13_2)$, $(13_3)$ and $(13_4)$. If constructed as described above, even in the case where the high conductivity value is shown, but there is no difference among the differential values of milk from the quarter mammae, these milk can be detected as abnormal one without exception, and thus the examination can be made more complete.

As the present invention is constituted as described heretofore, milk drawn from the quarter mammae can be checked continuously while the milking operation is being done. Consequently, the state of variation of the quality of milk can be checked by a continuous examination throughout the time of the milking operation.

Further, as the electrode is equipped in the trap, even if the milk from the quarter mamma flow intermittently or bubbles are caused in the flow way, the apparatus will not operate wrong.

As described hithertofor, the examination apparatus according to the present invention is attached to the milking machine for automatically sucking out milk from the cow. This apparatus can be attached to the machine of the claw type of course, also to that of the suspension type. Further, the apparatus can be attached to the machine of any scale such as a small one which draws milk from a milk cow at a time and a large one which treats several cows at a time.

What is claimed is:

1. An examination apparatus for milk drawn from the quarter mamma of a cow, comprising a flow passage for the milk drawn from each quarter mamma, a trap provided in each said flow passage, electrodes provided in each said trap, an electric conductivity measuring circuit connected to said electrodes in each said trap for measuring the electric conductivity of the milk therein, a minimum value selecting circuit connected to said electric conductivity measuring circuit for selecting the minimum conductivity value measured, a subtracting circuit connected to said electric conductivity measuring circuit and the minimum value selecting circuit for outputting the difference in electric conductivity of the milk from at least two of the quarter mammae, comparator circuit means for comparing the output of said subtracting circuit with at least one predetermined reference value, grouping circuit means for grouping corresponding outputs of said comparator circuit means and an indication means responsive to the output of said grouping circuit means for indicating the extent of the quality of the milk.

2. An examination apparatus for milk drawn from the quarter mamma of a cow as claimed in claim 1, wherein the comparator circuit means includes first comparator circuits to which an upper limit value is input as the reference value and other comparator circuits to which a lower limit value is input as the reference value, and wherein said indication means, when an output of the subtracting circuit is below the lower limit value, indicates the milk associated with such output is normal, when an output of the subtracting circuit is higher than the upper limit value, indicates the associated milk is abnormal, and, when an output is intermediate said upper and lower limit values, indicates the associated milk is quasi-abnormal.

3. An examination apparatus for milk drawn from the quarter mamma of a cow as claimed in claim 1 or claim 2, wherein the comparator circuit means includes a comparator circuit which produces an output when the minimum electric conductivity value from the minimum value selecting circuit exceeds a predetermined reference value, and wherein the indication means is directly driven by the output of said comparator circuit.

4. An examination apparatus for milk drawn from the quarter mamma of a cow as claimed in claim 1, wherein the subtracting circuit outputs difference values obtained by subtracting from the electric conductivity of the milk from the respective quarter mamma the minimum electric conductivity from the minimum value selecting circuit.

5. An examination apparatus for milk drawn from the quarter mamma of a cow as claimed in claim 1, wherein said electric conductivity measuring circuit includes a maximum value selecting circuit for selecting the maximum conductivity value measured, and wherein the subtracting circuit outputs a value obtained by subtracting the maximum electric conductivity value and the minimum electric conductivity value.

6. An examination apparatus for milk drawn from the quarter mamma of a cow, comprising:
a flow passage for the milk drawn from each quarter mamma;
electrodes provided in each said flow passage;
means cooperable with said electrodes for measuring the conductivity of the milk drawn from each quarter mamma;
subtractor means responsive to said conductivity measuring means for determining the difference in conductivity of the milk drawn from at least two of the quarter mamma;
comparator means responsive to said subtractor means for comparing said difference in conductivity to at least one predetermined reference value;
indicator means responsive to said comparator means for producing an indication when said difference in conductivity exceeds said predetermined reference value.

7. The apparatus of claim 6, wherein said conductivity measuring means includes minimum conductivity selecting means for selecting the minimum conductivity value measured, said subtractor means determines the difference between said minimum conductivity and the conductivity of the milk from each quarter mamma, said comparator means compares each said difference in conductivity to at least one predetermined reference value, and said indicator means produces said indication when any said difference in conductivity exceeds said predetermined reference value.

8. The apparatus according to claim 6, wherein said conductivity measuring means includes minimum conductivity selecting means for selecting the minimum conductivity value measured and maximum conductivity selecting means for selecting the maximum conductivity value measured, said subtractor means determining the difference between said maximum conductivity value and said minimum conductivity value.

9. The apparatus according to claim 7 or claim 8, including further comparator means for comparing said minimum conductivity value to a predetermined reference conductivity, and wherein said indicator means is responsive to said further comparator means for producing an indication when said minimum conductivity value is greater than said predetermined reference conductivity.

10. The apparatus of claim 6, wherein said comparator means compares said difference in conductivity to two said predetermined reference values, and wherein said indicator means produces a first said indication if said difference in conductivity is greater than one said predetermined reference value but less than the other said predetermined reference value and produces a second said indication if said difference value is greater than both of said predetermined reference values.

* * * * *